(12) United States Patent
Vanderbilt et al.

(10) Patent No.: US 8,454,689 B2
(45) Date of Patent: *Jun. 4, 2013

(54) BRUSH COPOLYMERS

(75) Inventors: David Paul Vanderbilt, Webster, NY (US); Paul L. Valint, Jr., Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 382 days.

This patent is subject to a terminal disclaimer.

(21) Appl. No.: 12/641,473

(22) Filed: Dec. 18, 2009

(65) Prior Publication Data

US 2010/0168852 A1 Jul. 1, 2010

Related U.S. Application Data

(60) Provisional application No. 61/203,885, filed on Dec. 30, 2008.

(51) Int. Cl.
*A61F 2/16* (2006.01)
*C08F 30/06* (2006.01)
*C08F 275/00* (2006.01)

(52) U.S. Cl.
USPC .......... 623/6.62; 525/242; 525/288; 523/113; 526/239

(58) Field of Classification Search
USPC ........... 525/242, 288, 298; 526/239; 523/103, 523/106, 113; 623/6.62; 351/160 R
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,055,378 A | 10/1977 | Feneberg et al. |
| 4,113,224 A | 9/1978 | Clark et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deicherte et al. |
| 4,197,266 A | 4/1980 | Clark et al. |
| 4,214,014 A | 7/1980 | Hofer et al. |
| 4,312,575 A | 1/1982 | Peyman et al. |
| 4,555,732 A | 11/1985 | Tuhro |
| 4,632,844 A | 12/1986 | Yanagihara |
| 4,740,533 A | 4/1988 | Su et al. |
| 4,910,277 A | 3/1990 | Bambury et al. |
| 4,954,587 A | 9/1990 | Mueller |
| 5,010,141 A | 4/1991 | Mueller |
| 5,034,461 A | 7/1991 | Lai et al. |
| 5,070,215 A | 12/1991 | Bambury et al. |
| 5,079,319 A | 1/1992 | Mueller |
| 5,260,000 A | 11/1993 | Wandu et al. |
| 5,271,875 A | 12/1993 | Appleton et al. |
| 5,310,779 A | 5/1994 | Lai |
| 5,321,108 A | 6/1994 | Kunzler et al. |
| 5,358,995 A | 10/1994 | Lai et al. |
| 5,387,662 A | 2/1995 | Kunzler et al. |
| 5,449,729 A | 9/1995 | Lai |
| 5,464,667 A | 11/1995 | Kohler et al. |
| 5,512,205 A | 4/1996 | Lai |
| 5,610,252 A | 3/1997 | Bambury et al. |
| 5,616,757 A | 4/1997 | Bambury et al. |
| 5,708,094 A | 1/1998 | Lai et al. |
| 5,710,302 A | 1/1998 | Kunzler et al. |
| 5,714,557 A | 2/1998 | Kunzler |
| 5,908,906 A | 6/1999 | Kunzler |
| 6,440,366 B1 | 8/2002 | Salpekar et al. |
| 6,582,754 B1 | 6/2003 | Pasic et al. |
| 7,988,988 B2 * | 8/2011 | Valint et al. .................... 424/427 |
| 2005/0203256 A1 * | 9/2005 | Destarac et al. ............. 525/337 |
| 2008/0151181 A1 | 6/2008 | Vanderbilt et al. |

FOREIGN PATENT DOCUMENTS

| | | |
|---|---|---|
| WO | WO 94/06485 | 3/1994 |
| WO | WO 95/04609 | 2/1995 |
| WO | WO 96/31792 | 10/1996 |
| WO | WO03/095502 | 11/2003 |
| WO | WO2007/061919 | 5/2007 |

OTHER PUBLICATIONS

Daintith, J. et al A Dictionary of Science 6th Edtion Oxford University Press, Oxford et al 2010 p. 231.*
International Search Report (PCT/ISA/210) and Written Opinion (PCT/ISA/237) mailed on Mar. 16, 2010.
Kahraman, G. et al. "Bioengineering polyfunctional copolymers." Polymer, Elsevier Science Publishers, vol. 45, No. 17, pp. 5813-5828, Aug. 5, 2004.
Lai, Yu-Chin, "The Role of Bulky Polysiloxanylalkyl Methacrylates in Polyurethane-Polysiloxane Hydrogels," Journal of Applied Polymer Science, vol. 60, 1193-1199 (1996).
A. T. Bell, Proc. Intl. Conf. Phenom. Ioniz. Gases, "Chemical Reaction in Nonequilibrium Plasmas", 19-33 (1977).
J. M. Tibbitt, R. Jensen, A. T. Bell, M. Shen, Macromolecules, "A Model for the Kinetics of Plasma Polymerization", 3, 648-653 (1977).
J. M. Tibbitt, M. Shen, A. T. Bell, J. Macromol. Sci.-Chem., "Structural Characterization of Plasma-Polymerized Hydrocarbons", A10, 1623-1648 (1976).
C. P. Ho, H. Yasuda, J. Biomed, Mater. Res., "Ultrathin coating of plasma polymer of methane applied on the surface of silicone contact lenses", 22, 919-937 (1988).
H. Kobayashi, A. T. Bell, M. Shen, Macromolecules, "Plasma Polymerization of Saturated and Unsaturated Hydrocarbons", 3, 277-283 (1974).
H. Yasuda, H. C. Marsh, M. O. Bumgarner, N. Morosoff, J. of Appl. Poly. Sci., "Polymerization of Organic Compounds in an Electroless Glow Discharge. VI. Acetylene with Unusual Co-monomers", 19, 2845-2858 (1975).

* cited by examiner

*Primary Examiner* — Irina S Zemel
*Assistant Examiner* — Jeffrey Lenihan
(74) *Attorney, Agent, or Firm* — John E. Thomas

(57) ABSTRACT

Brush copolymers containing (a) monomeric units derived from an ethylenically unsaturated monomer containing one or more boronic acid moieties and; and (b) monomeric units derived from an ethylenically unsaturated-containing hydrophilic macromonomer are disclosed.

12 Claims, No Drawings

BRUSH COPOLYMERS

This application claims the benefit of Provisional Patent Application No. 61/203,885 filed Dec. 30, 2008 which is incorporated by reference herein.

BACKGROUND OF THE INVENTION

1. Technical Field

The present invention generally relates to a brush copolymer and a biomedical device such as ophthalmic lenses having a brush copolymer coating on at least a portion of the surface thereof.

2. Description of Related Art

Medical devices such as ophthalmic lenses made from, for example, silicone-containing materials, have been investigated for a number of years. Such materials can generally be subdivided into two major classes, namely, hydrogels and non-hydrogels. Hydrogels can absorb and retain water in an equilibrium state, whereas non-hydrogels do not absorb appreciable amounts of water. Regardless of their water content, both hydrogel and non-hydrogel silicone medical devices tend to have relatively hydrophobic, non-wettable surfaces that have a high affinity for lipids. This problem is of particular concern with contact lenses.

Those skilled in the art have long recognized the need for modifying the surface of such silicone contact lenses so that they are compatible with the eye. It is known that increased hydrophilicity of the lens surface improves the wettability of the contact lens. This, in turn, is associated with improved wear comfort of contact lenses. Additionally, the surface of the lens can affect the lens's susceptibility to deposition, particularly the deposition of proteins and lipids resulting from tear fluid during lens wear. Accumulated deposition can cause eye discomfort or even inflammation. In the case of extended wear lenses (i.e., lenses used without daily removal of the lens before sleep), the surface is especially important, since extended wear lenses must be designed for high standards of comfort and biocompatibility over an extended period of time.

Silicone lenses have been subjected to plasma surface treatment to improve their surface properties, e.g., surfaces have been rendered more hydrophilic, deposit resistant, scratch-resistant, or otherwise modified. Examples of previously disclosed plasma surface treatments include subjecting the surface of a contact lens to a plasma containing an inert gas or oxygen (see, for example, U.S. Pat. Nos. 4,055,378; 4,122,942; and 4,214,014); various hydrocarbon monomers (see, for example, U.S. Pat. No. 4,143,949); and combinations of oxidizing agents and hydrocarbons such as water and ethanol (see, for example, WO 95/04609 and U.S. Pat. No. 4,632,844). U.S. Pat. No. 4,312,575 discloses a process for providing a barrier coating on a silicone or polyurethane lens by subjecting the lens to an electrical glow discharge (plasma) process conducted by first subjecting the lens to a hydrocarbon atmosphere followed by subjecting the lens to oxygen during flow discharge, thereby increasing the hydrophilicity of the lens surface.

U.S. Pat. No. 6,582,754 ("the '754 patent") discloses a process for coating a material surface involving the steps of (a) providing an organic bulk material having functional groups on its surface; (b) covalently binding to the surface of the bulk material a layer of a first compound having a first reactive group and an ethylenically unsaturated double bond by reacting the function groups on the surface of the bulk material with the first reactive group of the first compound; (c) copolymerizing, on the surface of the bulk material, a first hydrophilic monomer and a monomer comprising a second reactive group to form a coating comprising a plurality of primary polymer chains which are covalently bonded to the surface through the first compound, wherein each primary polymer chain comprises second reactive; (d) reacting the second reactive groups of the primary polymer chains with a second compound comprising an ethylenically unsaturated double bond and a third reactive group that is co-reactive with the second reactive group, to covalently bind the second compound to the primary polymer chains; and (e) graft-polymerizing a second hydrophilic monomer to obtain a branched hydrophilic coating on the surface of the bulk material, wherein the branched hydrophilic coating comprises the plurality of the primary polymer chains and a plurality of secondary chains each of which is covalently attached through the second compound to one of the primary chains. The process disclosed in the '754 patent is time consuming as it involves multiple steps and uses many reagents in producing the coating on the substrate.

Blister packages and glass vials are typically used to individually package each soft contact lens for sale to a customer. Saline or deionized water is commonly used to store the lens in the packages, as mentioned in various patents related to the packaging or manufacturing of contact lenses. Because lens material may tend to stick to itself and to the lens package, packaging solutions for blister packs have sometimes been formulated to reduce or eliminate lens folding and sticking; packaging solutions may include a polymer to improve comfort of the contact lens. Polyvinyl alcohol (PVA) has been used in contact lens packaging solutions. Additionally, U.S. Pat. No. 6,440,366 discloses contact lens packaging solutions comprising polyethylene oxide (PEO)/polypropylene oxide (PPO) block copolymers, especially poloxamers or poloxamines.

U.S. Patent Application Publication No. 20080151181 ("the '181 application), commonly assigned to assignee herein Bausch & Lomb Incorporated, discloses a contact lens having its surfaces coated with an inner layer and an outer layer, the inner layer comprising a polymer comprising monomeric units derived from an ethylenically unsaturated monomer containing a boronic acid moiety, and the outer layer comprising a diol. The '181 application further discloses that the diol layer includes at least one diol-terminated polymer member selected from the group consisting of diol-terminated polyvinyl pyrrolidinone, diol-terminated polyacrylamides, diol-terminated polyethylene oxides, and diol-terminated polyethylene oxide (PEO)/polypropylene oxide (PPO) block copolymers.

It would be desirable to provide improved surface modified biomedical devices having an optically clear, hydrophilic coating on the surface thereof that renders the device more biocompatible. In addition, it would also be desirable to form a coating on a contact lens having improved wettability and lubriciousness while also inhibiting attachment of microorganisms to the surface of the lens, thus making the lens more comfortable to wear for a longer period of time. In this manner, the biocompatibilized lens can be capable of continuous wear overnight, preferably for a week or more without adverse effects to the cornea.

SUMMARY OF THE INVENTION

In accordance with one embodiment of the present invention, a brush copolymer is provided comprising (a) monomeric units derived from an ethylenically unsaturated monomer containing one or more boronic acid moieties; and (b)

monomeric units derived from an ethylenically unsaturated-containing hydrophilic macromonomer.

In accordance with a second embodiment of the present invention, a brush copolymer is provided comprising monomeric units derived from an ethylenically unsaturated monomer containing one or more boronic acid moieties in the backbone of the polymer; and bristles of monomeric units derived from an ethylenically unsaturated-containing hydrophilic macromonomer.

In accordance with a third embodiment of the present invention, a biomedical device having a coating on at least a portion of a surface thereof is provided, the coating comprising a brush copolymer comprising (a) monomeric units derived from an ethylenically unsaturated monomer containing one or more boronic acid moieties; and (b) monomeric units derived from an ethylenically unsaturated-containing hydrophilic macromonomer.

In accordance with a fourth embodiment of the present invention, a method for making a biomedical device is provided, the method comprising exposing a biomedical device having a plurality of biomedical device surface functional groups to one or more brush copolymers comprising (a) monomeric units derived from an ethylenically unsaturated monomer containing one or more boronic acid moieties; and (b) monomeric units derived from an ethylenically unsaturated-containing hydrophilic macromonomer, thus forming a biocompatible surface on the biomedical device.

In accordance with a fifth embodiment of the present invention, a method for inhibiting adhesion of bacteria to a surface of a biomedical device is provided, the method comprising (a) providing a biomedical device having a coating on at least a portion of a surface thereof, the coating comprising a brush copolymer comprising (i) monomeric units derived from an ethylenically unsaturated monomer containing one or more boronic acid moieties; and (ii) monomeric units derived from an ethylenically unsaturated-containing hydrophilic macromonomer; and (b) inserting the biomedical device in the eye of a patient.

The boronic acid moieties in the backbone of the brush copolymer of the present invention bind to biomedical device surface functional groups on the surface of a biomedical device while the bristles of monomeric units derived from an ethylenically unsaturated-containing hydrophilic macromonomer provide a hydrophilic or lubricious (or both) surface. Accordingly, the brush copolymers of the present invention advantageously provide improved surface treated biomedical devices exhibiting a higher level of performance quality and/or comfort to the users due to their hydrophilic or lubricious (or both) surfaces. Hydrophilic and/or lubricious surfaces of the biomedical devices herein such as contact lenses substantially prevent or limit the adsorption of tear lipids and proteins on, and their eventual absorption into, the lenses, thus preserving the clarity of the contact lenses. This, in turn, preserves their performance quality thereby providing a higher level of comfort to the wearer. In addition, the brush copolymers of the present invention are believed to render the surface of the biomedical device more resistant to bacterial attachment.

DETAILED DESCRIPTION OF THE PREFERRED EMBODIMENTS

The present invention is directed to brush copolymers useful in treating the surface of a biomedical device intended for direct contact with body tissue or fluid. In general, "polymer brushes," contain polymer chains, one end of which is directly or indirectly tethered to a surface and another end of which is free to extend from the surface, somewhat analogous to the bristles of a brush. The brush copolymers of the present invention have at least one or more types of boronic acid polymer chains, which bind to biomedical device surface functional groups on the surface of a biomedical device, and one or more types of hydrophilic macromonomer polymer chains, which do not bind to biomedical device surface functional groups on the surface of a biomedical device. As used herein the terms "bound", "binding", or terms of similar import, refer to various chemical interactions such as, electrostatic, ionic, complexation, hydrogen bond or other interaction between the brush copolymer and at least the functionalities at the surface of the device which results in the association of the brush copolymer coating with the device. In one embodiment, the brush polymers of the present invention contain at least (a) monomeric units derived from an ethylenically unsaturated monomer containing one or more boronic acid moieties; and (b) monomeric units derived from an ethylenically unsaturated-containing hydrophilic macromonomer.

Representative examples of suitable ethylenically unsaturated monomers containing one or more boronic acid moieties include ethylenically unsaturated-containing alkyl boronic acids; ethylenically unsaturated-containing cycloalkyl boronic acids; ethylenically unsaturated-containing aryl boronic acids and the like and mixtures thereof. Preferred ethylenically unsaturated monomers having one or more boronic acid moieties include 4-vinylphenylboronic acid, 3-methacrylamidophenylboronic acid, 3-acrylamidophenylboronic acid and mixtures thereof.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, etc., and the like.

Representative examples of cycloalkyl groups for use herein include, by way of example, a substituted or unsubstituted non-aromatic mono or multicyclic ring system of about 3 to about 24 carbon atoms such as, for example, cyclopropyl, cyclobutyl, cyclopentyl, cyclohexyl, perhydronapththyl, adamantyl and norbornyl groups bridged cyclic group or spriro-bicyclic groups, e.g., sprio-(4,4)-non-2-yl and the like, optionally containing one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of the ethylenically unsaturated moiety of the ethylenically unsaturated monomer include, by way of example, (meth)acrylate-containing radicals, (meth)acrylamido-containing radicals, vinyl carbonate-containing radicals, vinylcarbamate-containing radicals, styrene-containing radicals, itaconate-containing radicals, vinyl-containing radicals, vinyloxy-containing radicals, fumarate-containing radicals, maleimide-containing radicals, vinylsulfonyl radicals and the like. As used herein, the term "(meth)" denotes an optional methyl substituent. Thus, for example, terms such as "(meth)acrylate" denotes either methacrylate or acrylate, and "(meth)acrylamide" denotes either methacrylamide or acrylamide.

In one embodiment, an ethylenically unsaturated moiety of the ethylenically unsaturated boronic acid-containing monomer is represented by the general formula:

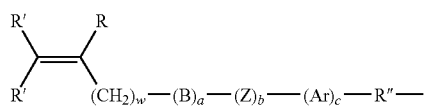

wherein R is hydrogen or a alkyl group having 1 to 6 carbon atoms such as methyl; each R' is independently hydrogen, an alkyl radical having 1 to 6 carbon atoms, or a —CO—Y—R'" radical wherein Y is —O—, —S— or —NH— and R'" is an alkyl radical having 1 to about 10 carbon atoms; R" is a linking group (e.g., a divalent alkenyl radical having 1 to about 12 carbon atoms); B denotes —O— or —NH—; Z denotes —CO—, —OCO— or —COO—; Ar denotes an aromatic radical having 6 to about 30 carbon atoms; w is 0 to 6; a is 0 or 1; b is 0 or 1; and c is 0 or 1. The ethylenically unsaturated-containing moiety can be attached to the boronic acid-containing monomers as pendent groups, terminal groups or both.

The brush copolymers further include monomeric units derived from an ethylenically unsaturated-containing hydrophilic macromonomer. As used herein, the term "macromonomer" denotes high molecular weight polymers that are prepared by free radical polymerization or controlled radical polymerization. In general, the hydrophilic macromonomers have a number average molecular weight of about 500 to about 200,000 and preferably from about 500 to about 20,000. The hydrophilic groups are derived from a hydrophilic monomer such as, for example, acrylamides such as N,N-dimethylacrylamide, N,N-dimethylmethacrylamide, and the like; acetamides such as N-vinyl-N-methyl acetamide, N-vinyl acetamide and the like; formamides such as N-vinyl-N-methyl formamide, N-vinyl formamide, and the like; cyclic lactams such as N-vinyl-2-pyrrolidone and the like; (meth)acrylated alcohols such as 2-hydroxyethyl methacrylate, 2-hydroxyethyl acrylate and the like; (meth)acrylated poly(ethyleneglycol)s and the like and mixtures thereof. The ethylenically unsaturated-containing moiety can be any of the ethylenically unsaturated-containing moieties discussed hereinabove. As one skilled in the art will readily appreciate, the ethylenically unsaturated-containing moiety can be attached to the hydrophilic monomer as a pendent group, terminal group or both.

In one embodiment, the hydrophilic macromonomers can be expeditiously prepared using techniques of controlled radical polymerization, i.e. by atom-transfer radical polymerization (ATRP) or reversible addition-fragmentation chain transfer (RAFT) polymerization RAFT polymerization employs a chain transfer agent that allows construction of hydrophilic macromonomers with a well-defined molecular weight distribution and narrow polydispersity. RAFT polymerization is particularly preferred because it is compatible with a wide variety of vinyl monomers. For example, hydroxy-functionalized xanthate RAFT agents such as 2-hydroxyethyl 2-(ethoxyxanthyl)propionate (HEEXP) can be used with monomers such as NVP (Scheme A) and carboxylate-functional trithiocarbonate RAFT agents such as 2-methyl 2-(dodecylthiocarbonylthio)propanoic acid (MDTCTPA) work well with more reactive monomers such as DMA (Scheme B). Other RAFT agent types such as dithiocarbamates and aliphatic or aromatic dithioesters may also be used depending on the type of vinyl monomer employed. RAFT agents having appropriate end group functionalities such as those illustrated in Schemes A, B and C, can be used to prepare the hydrophilic macromonomers for use in forming the brush copolymers of the present invention.

SCHEME A

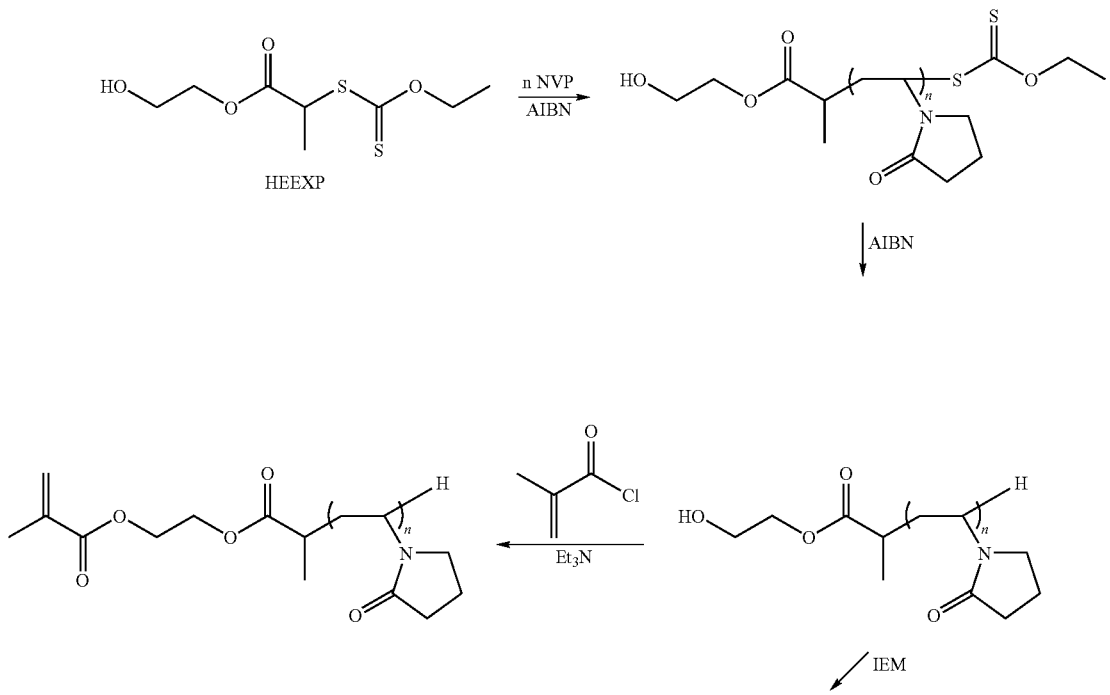

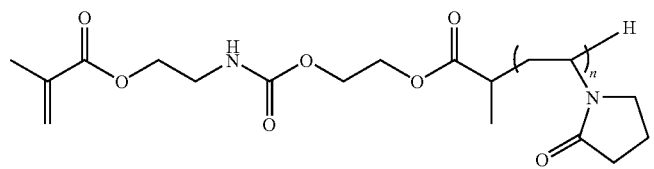
wherein n is from 5 to about 200 and preferably from 5 to about 20.
SCHEME B
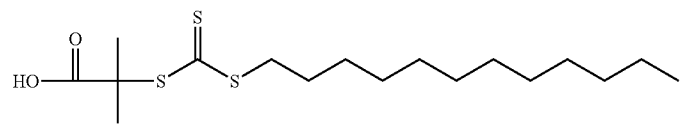
MDTCTPA
↓ n DMA
  AIBN
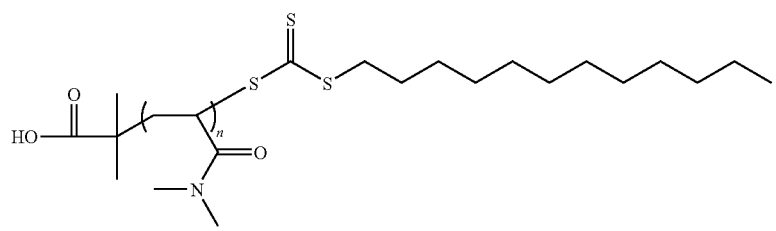
↓ AIBN
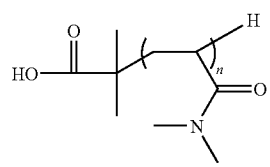
↓ GMA          ↓ HEMA
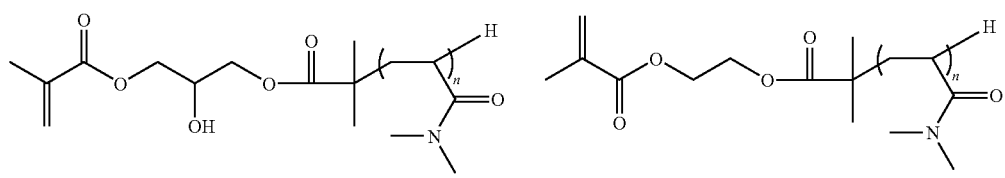
wherein n has the aforestated meanings.

SCHEME C

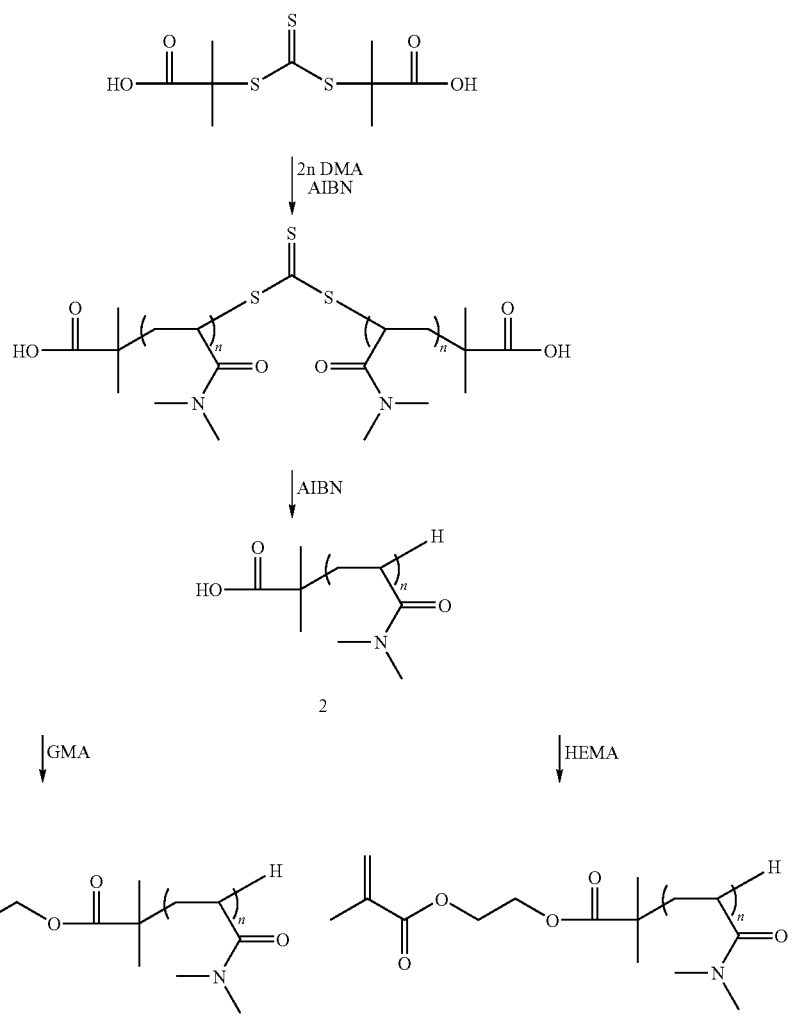

wherein n has the aforestated meanings.

In another embodiment, the ethylenically unsaturated hydrophilic macromonomers can be obtained by first (1) mixing the hydrophilic monomer with a suitable chain transfer agent; (2) adding a polymerization initiator; (3) and subjecting the monomer/initiator mixture to a source of heat. Suitable chain transfer agents include, but are not limited to, thioglycolic acid, mercaptoethanol; and the like. Typical initiators include free-radical-generating polymerization initiators of the type illustrated by acetyl peroxide, lauroyl peroxide, decanoyl peroxide, coprylyl peroxide, benzoyl peroxide, tertiary butyl peroxypivalate, sodium percarbonate, tertiary butyl peroctoate, and azobis-isobutyronitrile (AIBN). The level of initiator employed will vary within the range of 0.01 to 2 weight percent of the mixture of monomers. Usually, a mixture of the above-mentioned monomers is warmed with addition of a free-radical former.

The reaction can be carried out at a temperature of between about 50° C. to about 70° C. for about 12 to about 72 hours. The reaction can be carried out in the presence of a suitable solvent. Suitable solvents are in principle all solvents which dissolve the monomer used, for example, carboxamides such as dimethylformamide; polar aprotic solvents such as dimethyl sulfoxide; ketones such as acetone or cyclohexanone; ethers such as ethyl ether, tetrahydrofuran, dioxane; and hydrocarbons such as toluene and the like.

Next, the ethylenically unsaturated-containing moiety is introduced by using an excess of either acryloyl or methacryloyl chloride and in the presence of an amine scavenger such as triethylamine. The reaction can be carried out at room temperature. In one embodiment, the ethylenically unsaturated hydrophilic macromonomers can be prepared according to the method generally shown in Schemes D and E below.

SCHEME D

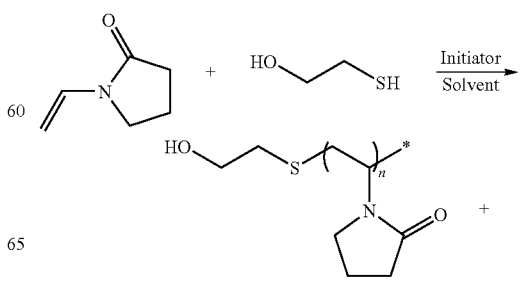

-continued

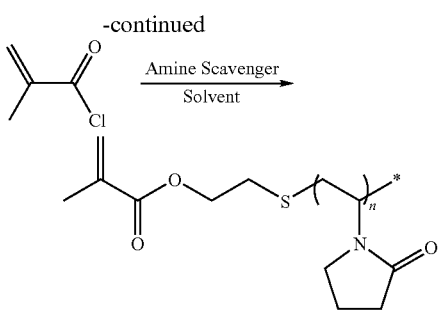

wherein n has the aforestated meanings.

SCHEME E

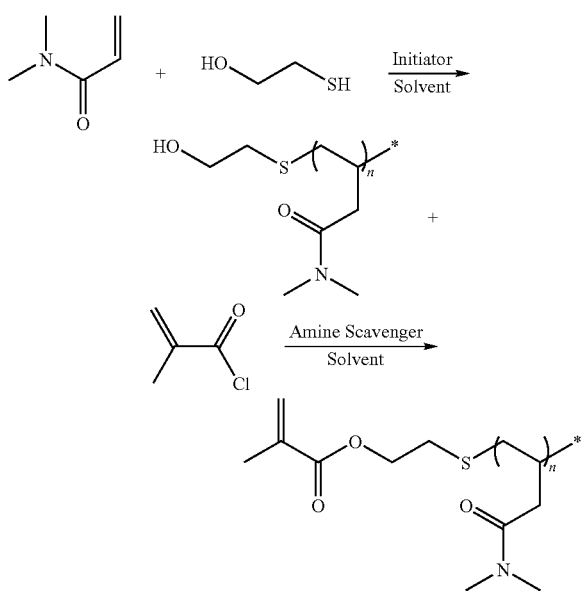

wherein n has the aforestated meanings.

The brush copolymers can further include a monomeric unit containing a tertiary-amine terminal moiety in the backbone of the polymer. Suitable monomers copolymerizable with the boronic acid monomer and hydrophilic macromonomer are ethylenically unsaturated monomers containing a tertiary-amine moiety. Representative examples include, but are not limited to, 2-(N,N-dimethyl)ethylamino(meth)acrylate, N42-(dimethylamino)ethyl (meth)acrylamide, N-[(3-dimethylamino)propyl](meth)acrylate, N-[3-dimethylamino)propyl](meth)acrylamide, vinylbenzyl-N,N-dimethylamine and the like and mixtures thereof.

The brush copolymers of the present invention may further include a monomeric unit containing a hydrophilic moiety in the backbone of the polymer. Representative examples include, but are not limited to, N,N-dimethylacrylamide, N,N-dimethylmethacrylamide and the like; acetamides such as N-vinyl-N-methyl acetamide and N-vinyl acetamide and the like; formamides such as N-vinyl-N-methyl formamide and N-vinyl formamide, and the like; 2cyclic lactams such as N-vinyl-2-pyrrolidone and the like; (meth)acrylated alcohols such as 2-hydroxyethyl methacrylate, 2-hydroxyethyl acrylate and the like; (meth)acrylated poly(ethyleneglycol)s and the like and mixtures thereof. The hydrophilic monomeric unit in the polymer, when used, ensures that the copolymer is water-soluble, thus avoiding the need to dissolve the copolymer in organic solvent when applying the polymer to the lens surface.

One class of brush copolymers are copolymers containing (a) monomeric units derived from an ethylenically unsaturated monomer containing one or more boronic acid moieties, (b) monomeric units derived from an ethylenically unsaturated hydrophilic macromonomer, (c) monomeric units derived from the ethylenically unsaturated monomer containing a tertiary-amine moiety, and (d) monomeric units derived from an ethylenically unsaturated hydrophilic monomer in an amount sufficient to render the copolymer water soluble. This class of copolymers may contain about 1 to about 20 mole percent of the boronic acid-containing monomeric units, and preferably about 2 to about 10 mole percent; about 1 to about 20 mole percent of monomeric units derived from an ethylenically unsaturated hydrophilic macromonomer, and preferably about 2 to about 10 mole percent, 1 to about 20 mole percent of the tertiary-amine-containing monomeric units, and preferably about 2 to about 10 mole percent; and 40 to about 90 mole percent of the hydrophilic monomeric units, and preferably about 50 to about 80 mole percent.

The brush copolymers of the present invention can be obtained by a polymerization reaction customary to the person skilled in the art. Typically, the polymers or chains are formed by subjecting a monomers/photo initiator mixture to a source of ultraviolet or actinic radiation and/or elevated temperature and curing the mixture. Typical polymerization initiators include free-radical-generating polymerization initiators such as acetyl peroxide, lauroyl peroxide, decanoyl peroxide, caprylyl peroxide, benzoyl peroxide, tertiary butyl peroxypivalate, sodium percarbonate, tertiary butyl peroctoate, and azobis-isobutyronitrile (AIBN). Typical ultraviolet free-radical initiators such as diethoxyacetophenone can also be used. The curing process will of course depend upon the initiator used and the physical characteristics of the monomer or monomer mixture such as viscosity. In any event, the level of initiator employed will vary within the range of about 0.001 to about 2 weight percent of the mixture of monomers.

Polymerization to form the resulting brush polymers can be carried out in the presence or absence of a solvent. Suitable solvents are in principle a solvent is capable of dissolving all of the monomers present in the monomer mixture. In a preferred embodiment, a suitable solvent is a polar solvent such as, for example, water; alcohols such as lower alkanols, for example, methanol and ethanol; and the like.

In another embodiment of the present invention, biomedical devices are provided which comprise the brush copolymers of the present invention at their surfaces. The brush copolymer may be provided over the entire surface of the biomedical device or over only a portion of the biomedical device surface. As used herein, the term "biomedical device" shall be understood to mean any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The preferred biomedical devices are ophthalmic devices, particularly contact lenses, and most particularly contact lenses made from silicone hydrogels.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

The biomedical devices to be surface modified according to the present invention can be any material known in the art capable of forming a biomedical device as described above. In one embodiment, a biomedical device includes devices formed from material not hydrophilic per se. Such devices are formed from materials known in the art and include, by way of example, polysiloxanes, perfluoropolyethers, fluorinated poly(meth)acrylates or equivalent fluorinated polymers derived, e.g., from other polymerizable carboxylic acids, polyalkyl (meth)acrylates or equivalent alkylester polymers derived from other polymerizable carboxylic acids, or fluorinated polyolefins, such as fluorinated ethylene propylene polymers, or tetrafluoroethylene, preferably in combination with a dioxol, e.g., perfluoro-2,2-dimethyl-1,3-dioxol. Representative examples of suitable bulk materials include, but are not limited to, Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to about 73 mol % of perfluoro-2,2-dimethyl-1,3-dioxol and about 37 to about 27 mol % of tetrafluoroethylene, or of about 80 to about 90 mol % of perfluoro-2,2-dimethyl-1,3-dioxol and about 20 to about 10 mol % of tetrafluoroethylene.

In another embodiment, a biomedical device includes devices formed from material hydrophilic per se, since reactive groups, e.g., carboxy, carbamoyl, sulfate, sulfonate, phosphate, amine, ammonium or hydroxy groups, are inherently present in the material and therefore also at the surface of a biomedical device manufactured therefrom. Such devices are formed from materials known in the art and include, by way of example, polyhydroxyethyl acrylate, polyhydroxyethyl methacrylate, polyvinyl pyrrolidone (PVP), polyacrylic acid, polymethacrylic acid, polyacrylamide, polydimethylacrylamide (DMA), polyvinyl alcohol and the like and copolymers thereof, e.g., from two or more monomers selected from hydroxyethyl acrylate, hydroxyethyl methacrylate, N-vinyl pyrrolidone, acrylic acid, methacrylic acid, acrylamide, dimethyl acrylamide, vinyl alcohol and the like. Representative examples of suitable bulk materials include, but are not limited to, Polymacon, Tefilcon, Methafilcon, Deltafilcon, Bufilcon, Phemfilcon, Ocufilcon, Focofilcon, Etafilcon, Hefilcon, Vifilcon, Tetrafilcon, Perfilcon, Droxifilcon, Dimefilcon, Isofilcon, Mafilcon, Nelfilcon, Atlafilcon and the like. Examples of other suitable bulk materials include Balafilcon A, Hilafilcon A, Alphafilcon A, Bilafilcon B and the like.

In another embodiment, biomedical devices to be surface modified according to the present invention include devices which are formed from material which are amphiphilic segmented copolymers containing at least one hydrophobic segment and at least one hydrophilic segment which are linked through a bond or a bridge member.

It is particularly useful to employ biocompatible materials herein including both soft and rigid materials commonly used for ophthalmic lenses, including contact lenses. In general, non-hydrogel materials are hydrophobic polymeric materials that do not contain water in their equilibrium state. Typical non-hydrogel materials comprise silicone acrylics, such as those formed bulky silicone monomer (e.g., tris(trimethylsiloxy)silylpropyl methacrylate, commonly known as "TRIS" monomer), methacrylate end-capped poly(dimethylsiloxane) prepolymer, or silicones having fluoroalkyl side groups (polysiloxanes are also commonly known as silicone polymers).

On the other hand, hydrogel materials comprise hydrated, cross-linked polymeric systems containing water in an equilibrium state. Hydrogel materials contain about 5 weight percent water or more (up to, for example, about 80 weight percent). The preferred hydrogel materials, include silicone hydrogel materials. In one preferred embodiment, materials include vinyl functionalized polydimethylsiloxanes copolymerized with hydrophilic monomers as well as fluorinated methacrylates and methacrylate functionalized fluorinated polyethylene oxides copolymerized with hydrophilic monomers. Representative examples of suitable materials for use herein include those disclosed in U.S. Pat. Nos. 5,310,779; 5,387,662; 5,449,729; 5,512,205; 5,610,252; 5,616,757; 5,708,094; 5,710,302; 5,714,557 and 5,908,906, the contents of which are incorporated by reference herein.

In one embodiment, hydrogel materials for biomedical devices, such as contact lenses, can contain a hydrophilic monomer such as one or more unsaturated carboxylic acids, vinyl lactams, amides, polymerizable amines, vinyl carbonates, vinyl carbamates, oxazolone monomers, copolymers thereof and the like and mixtures thereof. Useful amides include acrylamides such as N,N-dimethylacrylamide and N,N-dimethylmethacrylamide. Useful vinyl lactams include cyclic lactams such as N-vinyl-2-pyrrolidone. Examples of other hydrophilic monomers include hydrophilic prepolymers such as poly(alkene glycols) functionalized with polymerizable groups. Examples of useful functionalized poly(alkene glycols) include poly(diethylene glycols) of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. In another embodiment, a hydrogel material can contain a siloxane-containing monomer and at least one of the aforementioned hydrophilic monomers and/or prepolymers.

Non-limited examples of hydrophobic monomers are $C_1$-$C_{20}$ alkyl and $C_3$-$C_{20}$ cycloalkyl (meth)acrylates, substituted and unsubstituted aryl (meth)acrylates (wherein the aryl group comprises 6 to 36 carbon atoms), (meth) acrylonitrile, styrene, lower alkyl styrene, lower alky vinyl ethers, and $C_2$-$C_{10}$ perfluoroalkyl (meth)acrylates and correspondingly partially fluorinate (meth)acrylates.

A wide variety of materials can be used herein, and silicone hydrogel contact lens materials are particularly preferred. Silicone hydrogels generally have a water content greater than about 5 weight percent and more commonly between about 10 to about 80 weight percent. Such materials are usually prepared by polymerizing a mixture containing at least one silicone-containing monomer and at least one hydrophilic monomer. Typically, either the silicone-containing monomer or the hydrophilic monomer functions as a crosslinking agent (a crosslinker being defined as a monomer having multiple polymerizable functionalities) or a separate crosslinker may be employed. Applicable silicone-containing monomers for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth)acrylic monomer is represented by the structure of Formula I:

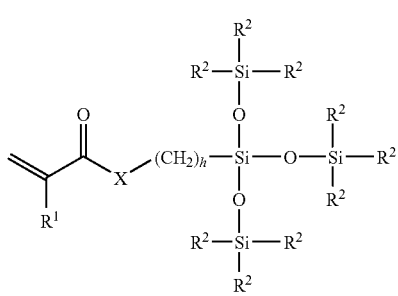

(I)

wherein X denotes —O— or —NR— wherein R denotes hydrogen or a $C_1$-$C_4$ alkyl; each $R^1$ independently denotes hydrogen or methyl; each $R^2$ independently denotes a lower alkyl radical, phenyl radical or a group represented by

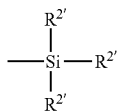

wherein each $R^{2'}$ independently denotes a lower alkyl or phenyl radical; and h is 1 to 10

Representative examples of other applicable silicon-containing monomers includes, but are not limited to, bulky polysiloxanylalkyl carbamate monomers as generally depicted in Formula Ia:

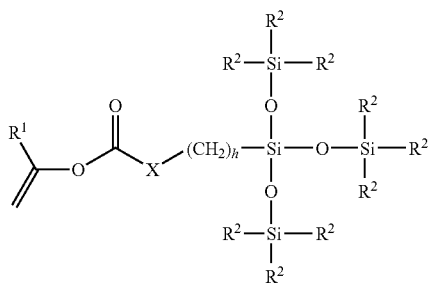

(Ia)

wherein X denotes -NR—; wherein R denotes hydrogen or a $C_1$-$C_4$ alkyl; $R^1$ denotes hydrogen or methyl; each $R^2$ independently denotes a lower alkyl radical, phenyl radical or a group represented by

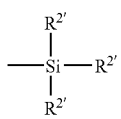

wherein each $R^{2'}$ independently denotes a lower alkyl or phenyl radical; and h is 1 to 10, and the like.

Examples of bulky monomers are 3-methacryloyloxypropyltris(trimethyl-siloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyl-disiloxane; 3-(trimethylsilyl)propyl vinyl carbonate; 3-vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like and mixtures thereof.

Another class of silicon-containing monomers includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulae II and III:

  (II)

  (III)

wherein:

D independently denotes an alkyl diradical, an alkyl cycloalkyl diradical, a cycloalkyl diradical, an aryl diradical or an alkylaryl diradical having 6 to about 30 carbon atoms;

G independently denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A independently denotes a divalent polymeric radical of Formula IV:

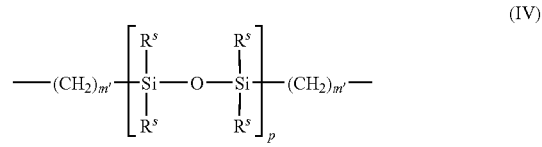

(IV)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

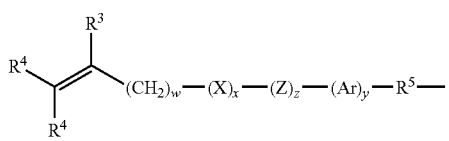
(V)

wherein:
$R^3$ is hydrogen or methyl;
$R^4$ is hydrogen, an alkyl radical having 1 to 6 carbon atoms, or a —CO—Y—$R^6$ radical wherein Y is —O—, —S— or —NH—;
$R^5$ is a divalent alkylene radical having 1 to about 10 carbon atoms;
$R^6$ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.

A preferred silicone-containing urethane monomer is represented by Formula VI:

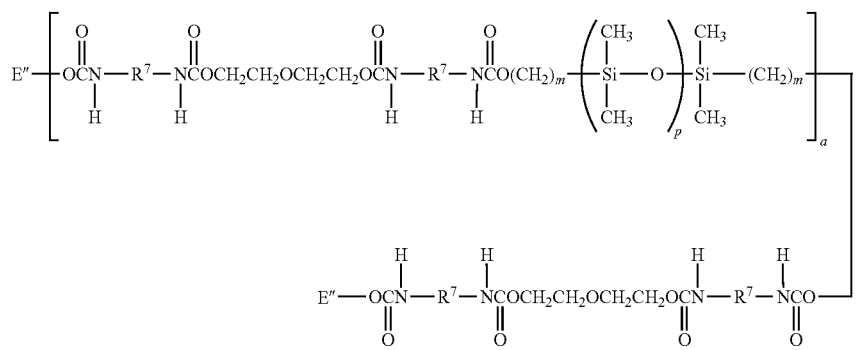

wherein m is at least 1 and is preferably 3 or 4, a is at least 1 and preferably is 1, p is a number which provides a moiety weight of about 400 to about 10,000 and is preferably at least about 30, $R^7$ is a diradical of a diisocyanate after removal of the isocyanate group, such as the diradical of isophorone diisocyanate, and each E" is a group represented by:

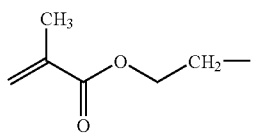

In another embodiment of the present invention, a silicone hydrogel material comprises (in bulk, that is, in the monomer mixture that is copolymerized) about 5 to about 50 percent, and preferably about 10 to about 25, by weight of one or more silicone macromonomers, about 5 to about 75 percent, and preferably about 30 to about 60 percent, by weight of one or more polysiloxanylalkyl (meth)acrylic monomers, and about 10 to about 50 percent, and preferably about 20 to about 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 discloses additional unsaturated groups, including acryloxy or methacryloxy. Fumarate-containing materials such as those disclosed in U.S. Pat. Nos. 5,310,779; 5,449,729 and 5,512,205 are also useful substrates in accordance with the invention. The silane macromonomer may be a silicon-containing vinyl carbonate or vinyl carbamate or a polyurethane-polysiloxane having one or more hard-soft-hard blocks and end-capped with a hydrophilic monomer.

Another class of representative silicone-containing monomers includes fluorinated monomers. Such monomers have been used in the formation of fluorosilicone hydrogels to reduce the accumulation of deposits on contact lenses made therefrom, as disclosed in, for example, U.S. Pat. Nos. 4,954,587; 5,010,141 and 5,079,319. Also, the use of silicone-containing monomers having certain fluorinated side groups, i.e., —($CF_2$)—H, have been found to improve compatibility between the hydrophilic and silicone-containing monomeric units. See, e.g., U.S. Pat. Nos. 5,321,108 and 5,387,662.

The above silicone materials are merely exemplary, and other materials for use as substrates that can benefit by being coated with the hydrophilic coating composition according to the present invention and have been disclosed in various publications and are being continuously developed for use in contact lenses and other medical devices can also be used. For example, a biomedical device can be formed from at least a cationic monomer such as cationic silicone-containing monomer or cationic fluorinated silicone-containing monomers.

Contact lenses for application of the present invention can be manufactured employing various conventional techniques, to yield a shaped article having the desired posterior and anterior lens surfaces. Spincasting methods are disclosed in U.S. Pat. Nos. 3,408,429 and 3,660,545; and static casting methods are disclosed in U.S. Pat. Nos. 4,113,224, 4,197,266 and 5,271,876. Curing of the monomeric mixture may be followed by a machining operation in order to provide a contact lens having a desired final configuration. As an example, U.S. Pat. No. 4,555,732 discloses a process in which an excess of a monomeric mixture is cured by spincasting in a mold to form a shaped article having an anterior lens surface and a relatively large thickness. The posterior surface of the cured spincast article is subsequently lathe cut to provide a contact lens having the desired thickness and posterior lens surface. Further machining operations may follow the lathe cutting of the lens surface, for example, edge-finishing operations.

Typically, an organic diluent is included in the initial monomeric mixture in order to minimize phase separation of polymerized products produced by polymerization of the monomeric mixture and to lower the glass transition temperature of the reacting polymeric mixture, which allows for a more efficient curing process and ultimately results in a more uniformly polymerized product. Sufficient uniformity of the initial monomeric mixture and the polymerized product is of particular importance for silicone hydrogels, primarily due to the inclusion of silicone-containing monomers which may tend to separate from the hydrophilic comonomer.

Suitable organic diluents include, for example, monohydric alcohols such as $C_6$-$C_{10}$ straight-chained aliphatic monohydric alcohols, e.g., n-hexanol and n-nonanol; diols such as ethylene glycol; polyols such as glycerin; ethers such as diethylene glycol monoethyl ether; ketones such as methyl ethyl ketone; esters such as methyl enanthate; and hydrocarbons such as toluene. Preferably, the organic diluent is sufficiently volatile to facilitate its removal from a cured article by evaporation at or near ambient pressure.

Generally, the diluent may be included at about 5 to about 60 percent by weight of the monomeric mixture, with about 10 to about 50 percent by weight being especially preferred. If necessary, the cured lens may be subjected to solvent removal, which can be accomplished by evaporation at or near ambient pressure or under vacuum. An elevated temperature can be employed to shorten the time necessary to evaporate the diluent.

Following removal of the organic diluent, the lens can then be subjected to mold release and optional machining operations. The machining step includes, for example, buffing or polishing a lens edge and/or surface. Generally, such machining processes may be performed before or after the article is released from a mold part. As an example, the lens may be dry released from the mold by employing vacuum tweezers to lift the lens from the mold.

As one skilled in the art will readily appreciate, biomedical device surface functional groups of the biomedical device according to the present invention may be inherently present at the surface of the device. However, if the biomedical device contains too few or no functional groups, the surface of the device can be modified by known techniques, for example, plasma chemical methods (see, for example, WO 94/06485), or conventional functionalization with groups such as —OH, or —$CO_2H$. Suitable biomedical device surface functional groups of the biomedical device include a wide variety of groups well known to the skilled artisan. Representative examples of such functional groups include, but are not limited to, hydroxy groups, c is 1,2-diols, c is 1,3-diols, a hydroxy acid groups (e.g., sialic acid, salicylic acid), carboxylic acids, di-carboxylic acids, catechols, silanols, silicates and the like.

In a preferred embodiment, the foregoing biomedical devices are subjected to an oxidative surface treatment such as corona discharge or plasma oxidation followed by treatment with the brush copolymers of the present invention. For example, a biomedical device such as a silicone hydrogel formulation containing hydrophilic polymers, such as poly (N,N-dimethylacrylamide) or poly(N-vinylpyrrolidinone), is subjected to an oxidative surface treatment to form at least silicates on the surface of the lens and then the lens is treated with an aqueous solution containing the brush copolymer of the present invention to render a lubricious, stable, highly wettable brush copolymer based surface coating. The complexation treatment is advantageously performed under autoclave conditions (sterilization conditions).

The standard process such as a plasma process (also referred to as "electrical glow discharge processes") provides a thin, durable surface upon the biomedical device prior to binding the brush copolymer to at least a portion of the surface thereof. Examples of such plasma processes are provided in U.S. Pat. Nos. 4,143,949; 4,312,575; and 5,464,667.

Although plasma processes are generally well known in the art, a brief overview is provided below. Plasma surface treatments involve passing an electrical discharge through a gas at low pressure. The electrical discharge may be at radio frequency (typically 13.56 MHz), although microwave and other frequencies can be used. Electrical discharges produce ultraviolet (UV) radiation, in addition to being absorbed by atoms and molecules in their gas state, resulting in energetic electrons and ions, atoms (ground and excited states), molecules, and radicals. Thus, a plasma is a complex mixture of atoms and molecules in both ground and excited states, which reach a steady state after the discharge is begun. The circulating electrical field causes these excited atoms and molecules to collide with one another as well as the walls of the chamber and the surface of the material being treated.

The deposition of a coating from a plasma onto the surface of a material has been shown to be possible from high-energy plasmas without the assistance of sputtering (sputter-assisted deposition). Monomers can be deposited from the gas phase and polymerized in a low pressure atmosphere (about 0.005 to about 5 torr, and preferably about 0.001 to about 1 torr) onto a substrate utilizing continuous or pulsed plasmas, suitably as high as about 1000 watts. A modulated plasma, for example, may be applied about 100 milliseconds on then off. In addition, liquid nitrogen cooling has been utilized to condense vapors out of the gas phase onto a substrate and subsequently use the plasma to chemically react these materials with the substrate. However, plasmas do not require the use of external cooling or heating to cause the deposition. Low or high wattage (e.g., about 5 to about 1000, and preferably about 20 to about 500 watts) plasmas can coat even the most chemical-resistant substrates, including silicones.

After initiation by a low energy discharge, collisions between energetic free electrons present in the plasma cause the formation of ions, excited molecules, and free-radicals. Such species, once formed, can react with themselves in the gas phase as well as with further ground-state molecules. The plasma treatment may be understood as an energy dependent process involving energetic gas molecules. For chemical reactions to take place at the surface of the lens, one needs the required species (element or molecule) in terms of charge state and particle energy. Radio frequency plasmas generally produce a distribution of energetic species. Typically, the "particle energy" refers to the average of the so-called Boltzman-style distribution of energy for the energetic species. In a low-density plasma, the electron energy distribution can be related by the ratio of the electric field strength sustaining the plasma to the discharge pressure (E/p). The plasma power density P is a function of the wattage, pressure, flow rates of gases, etc., as will be appreciated by the skilled artisan. Background information on plasma technology, hereby incorporated by reference, includes the following: A. T. Bell, Proc. Intl. Conf. Phenom. Ioniz. Gases, "*Chemical Reaction in Nonequilibrium Plasmas*", 19-33 (1977); J. M. Tibbitt, R. Jensen, A. T. Bell, M. Shen, Macromolecules, "A Model for the Kinetics of Plasma Polymerization", 3, 648-653 (1977); J. M. Tibbitt, M. Shen, A. T. Bell, J. Macromol. Sci.-Chem., "*Structural Characterization of Plasma-Polymerized Hydrocarbons*", A10, 1623-1648 (1976); C. P. Ho, H. Yasuda, J. Biomed. Mater. Res., "*Ultrathin coating of plasma polymer of methane applied on the surface of silicone contact lenses*", 22, 919-937 (1988); H. Kobayashi, A. T. Bell, M. Shen, Macromolecules, "*Plasma Polymerization of Saturated and Unsaturated Hydrocarbons*", 3, 277-283 (1974); R. Y. Chen, U.S. Pat. No. 4,143,949, Mar. 13, 1979, "*Process for Putting*

*a Hydrophilic Coating on a Hydrophobic Contact lens*"; and H. Yasuda, H. C. Marsh, M. O. Bumgarner, N. Morosoff, J. of Appl. Poly. Sci., *"Polymerization of Organic Compounds in an Electroless Glow Discharge. VI. Acetylene with Unusual Co-monomers"*, 19, 2845-2858 (1975).

Based on this previous work in the field of plasma technology, the effects of changing pressure and discharge power on the rate of plasma modification can be understood. The rate generally decreases as the pressure is increased. Thus, as pressure increases the value of E/p, the ratio of the electric field strength sustaining the plasma to the gas pressure decreases and causes a decrease in the average electron energy. The decrease in electron energy in turn causes a reduction in the rate coefficient of all electron-molecule collision processes. A further consequence of an increase in pressure is a decrease in electron density. Providing that the pressure is held constant, there should be a linear relationship between electron density and power.

In practice, contact lenses are surface-treated by placing them, in their unhydrated state, within an electric glow discharge reaction vessel (e.g., a vacuum chamber). Such reaction vessels are commercially available. The lenses may be supported within the vessel on an aluminum tray (which acts as an electrode) or with other support devices designed to adjust the position of the lenses. The use of a specialized support devices which permit the surface treatment of both sides of a lens are known in the art and may be used herein.

As mentioned above, the surface of the lens, for example, a silicone hydrogel continuous-wear lens is initially treated, e.g., oxidized, by the use of a plasma to render the subsequent brush copolymer surface deposition more adherent to the lens. Such a plasma treatment of the lens may be accomplished in an atmosphere composed of a suitable media, e.g., an oxidizing media such as oxygen, air, water, peroxide, $O_2$ (oxygen gas), etc., or appropriate combinations thereof, typically at an electric discharge frequency of about 13.56 Mhz, preferably between about 20 to about 500 watts at a pressure of about 0.1 to about 1.0 torr, preferably for about 10 seconds to about 10 minutes or more, more preferably about 1 to about 10 minutes. It is preferred that a relatively "strong" plasma is utilized in this step, for example, ambient air drawn through a five percent (5%) hydrogen peroxide solution. Those skilled in the art will know other methods of improving or promoting adhesion for bonding of the subsequent brush copolymer layer.

The biomedical device is then subjected to a surface treatment in accordance with the present invention. In general, the biomedical device such as a wettable silicone-based hydrogel lens is contacted with a solution containing at least one or more of the brush copolymers of the present invention, whereby the brush copolymer forms a complex with the plurality of biomedical device surface functional groups on the surface of the biomedical device. The biomedical devices can either be contacted with the solution containing at least the brush copolymers directly in the mold assembly or the biomedical device can be released from the mold assembly and then contacted with the solution. The solutions can be water-based solutions containing the brush copolymers and render a lubricious, stable, highly wettable surface. The complexation treatment is advantageously performed under autoclave conditions.

In one embodiment, the biomedical device is transferred to an individual lens package containing a buffered saline solution containing at least the brush copolymers of the present invention. Other components can be in the solutions as known in the art, e.g., tonicity agents, chelating agents, wetting agents and the like. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

The following examples are provided to enable one skilled in the art to practice the invention and are merely illustrative of the invention. The examples should not be read as limiting the scope of the invention as defined in the claims.

In the examples, the following abbreviations are used.
PVP: poly(vinyl pyrrolidone)
DMA: N,N-dimethylacrylamide
DMAPMA: N-[3-(dimethylamino)propyl]methacrylamide
NVP: N-vinyl-2-pyrrolidone
Vazo™ 64: azo bis-isobutylnitrile (AIBN)
THF: tetrahydrofuran
EDTA: ethylenediaminetetraacetic acid

EXAMPLE 1

Preparation of Methacrylated PVP Macromer

To a 1-L 3-neck round bottom flask containing a magnetic stir bar, water-cooled condenser and thermocouple was added 0.177 g AIBN (0.30-wt % based on total weight of NVP), 4.22 g (10-mol % based on NVP, Aldrich No. M2650) of 2-mercaptoethanol and 60 g of distilled NVP (Aldrich Cat. No. V3409). The mixture was dissolved by the addition of 250 mL of anhydrous THF to the flask. Next, the solution was sparged with argon for at least 10 minutes before gradual heating to 60° C. The sparging was discontinued when the solution reached 40 to 45° C. and the flask was subsequently maintained under argon backpressure. After 72 hours the heating was discontinued at which point the room temperature (RT) solution was opened to the atmosphere through a drying tube containing Drierite. Triethylamine (8.65 mL, 1.15 equivalents based on mercaptoethanol, Aldrich Cat. No. 471283) was added to the flask, whereupon some of the dissolved polymer precipitated. The solution was stirred at RT until all of the polymer redissolved. Methacryloyl chloride (5.75 mL, 1.10 equiv., Aldrich Cat. No. 523216) was then added in one portion, and the solution was allowed to stir at RT overnight. Triethylamine hydrochloride was removed from the solution by vacuum filtration. The filtered solution was added dropwise to 6-L of mechanically stirred ethyl ether. The solid was collected by vacuum filtration and the product dried in vacuo at RT for a minimum of 18 hours to provide 54 g of white prills. The number average molecular weight of methacrylated PVP was estimated to be 1200 Daltons.

EXAMPLE 2

Preparation of PVP Brush Polymer

To a 1-L 3-neck round bottom flask containing a magnetic stir bar, water-cooled condenser and thermocouple was added 0.152 g AIBN (0.40-wt % based on total weight of monomers), 1.21 g (4.25-mol %, Combi-Blocks No. BB-3222) of 3-methacrylamidophenylboronic acid, 25.0 g of the methacrylated PVP macromer of Example 1 (15 mol %), 2.01 g (8.5 mol %, Aldrich Cat. No. 409-472-1L) of deinhibited and distilled DMAPMA and 9.95 g (72.25-mol %, Aldrich Cat. No. 274135-500 mL) of distilled DMA. The mixture was dissolved by addition of 200-mL of methanol to the flask. The solution was sparged with argon for at least 10 minutes before gradual heating to 60° C. The sparging was discontinued when the solution reached 40 to 45° C. and the flask was subsequently maintained under argon backpressure. After 72 hours heating was discontinued at which point the cooled solution was added drop wise to 6 L of mechanically stirred ethyl ether. The precipitate was then isolated by vacuum filtration. The solid was dried in vacuo at 95° C. for a minimum of 18 hours. The solid was reprecipitated by dissolution in 150 mL methanol and drop wise addition into 6 L of stirred ethyl ether. The final polymer mass was determined after vacuum drying at 95° C. to a constant mass.

EXAMPLE 3

Preparation of Methacrylated DMA Macromer

To a 1-L 3-neck round bottom flask containing a magnetic stir bar, water-cooled condenser and thermocouple was added 0.177 g AIBN (0.30-wt % based on total weight of DMA), 4.73 g (10-mol % based on DMA, Aldrich No. M2650) of 2-mercaptoethanol and 60 g of distilled DMA (Aldrich Cat. No. 274135). The mixture was dissolved by the addition of 250 mL of anhydrous THF to the flask. The solution was sparged with argon for at least 10 minutes before gradual heating to 60° C. The sparging was discontinued when the solution reached 40 to 45° C. and the flask was subsequently maintained under argon backpressure. After 72 hours heating was discontinued at which point the RT solution was opened to the atmosphere through a drying tube containing Drierite. Triethylamine (9.70 mL, 1.15 equivalents based on mercaptoethanol, Aldrich Cat. No. 471283) was added to the flask, whereupon some of the dissolved polymer precipitated. The solution was stirred at RT until all of the polymer redissolved. Methacryloyl chloride (6.45 mL, 1.10 equiv., Aldrich Cat. No. 523216) was then added in one portion, and the solution was allowed to stir at RT overnight. Triethylamine hydrochloride was removed from the solution by vacuum filtration. The filtered solution was added dropwise to 6 L of mechanically stirred ethyl ether. The solid was collected by vacuum filtration and the product dried in vacuo at RT for a minimum of 18 hours. The number average molecular weight of methacrylated DMA macromer was estimated to be 1100 Daltons.

EXAMPLE 4

Preparation of DMA Brush Polymer

To a 1-L 3-neck round bottom flask containing a magnetic stir bar, water-cooled condenser and thermocouple was added 0.132 g AIBN (0.28-wt % based on total weight of monomers), 2.10 g (4.5-mol %, Combi-Blocks No. BB-3222) of 3-methacrylamidophenylboronic acid, 25.0 g of the methacrylated DMA macromer of Example 3 (10 mol %), 3.48 g (9.0-mol %, Aldrich Cat. No. 409-472-1L) of deinhibited and distilled DMAPMA and 17.24 g (76.5-mol %, Aldrich Cat. No. 274135-500 mL) of distilled DMA. The monomers and initiator were dissolved by addition of 200-mL of methanol to the flask. The solution was sparged with argon for at least 10 minutes before gradual heating to 60° C. The sparging was discontinued when the solution reached 40 to 45° C. and the flask was subsequently maintained under argon backpressure. After 72 hours heating was discontinued, at which point the cooled solution was added drop wise to 6 L of mechanically stirred ethyl ether. The precipitate was isolated by vacuum filtration. The solid was dried in vacuo at 95° C. for a minimum of 18 hours. The solid was then reprecipitated by dissolution in 150-mL methanol and drop wise addition into 6-L of stirred ethyl ether. The final polymer mass was determined after vacuum drying at 95° C. to a constant mass.

EXAMPLE 5

Contact lenses made of Balafilcon A are cast and processed under standard manufacturing procedures. Balafilcon A is a copolymer comprised of 3-[tris(tri-methylsiloxy)silyl]propyl vinyl carbamate, N-vinyl-2-pyrrolidone (NVP), 1,3-bis[4-vinyloxycarbonyloxy)but-1-yl]polydimethylsiloxane and N-vinyloxycarbonyl alanine. All Balafilcon A lenses are air-plasma treated prior to exposure to the brush copolymer.

For coating with the brush copolymer of Example 2, each lens is placed in a polypropylene blister package containing 3.8-mL of a 100 or 250 ppm (w/v) solution of the brush copolymer dissolved in borate-buffered saline (BBS) containing 300 ppm EDTA. The blisters are sealed is sealed with foil lidstock and autoclaved at 121° C. for 30 minutes.

EXAMPLE 6

Contact lenses made of Balafilcon A are cast and processed under standard manufacturing procedures. Balafilcon A is a copolymer comprised of 3-[tris(tri-methylsiloxy)silyl]propyl vinyl carbamate, N-vinyl-2-pyrrolidone (NVP), 1,3-bis[4-vinyloxycarbonyloxy)but-1-yl]polydimethylsiloxane and N-vinyloxycarbonyl alanine. All Balafilcon A lenses are air-plasma treated prior to exposure to the brush copolymer.

For coating with the brush copolymer of Example 4, each lens is placed in a polypropylene blister package containing 3.8-mL of a 100 or 250 ppm (w/v) solution of the brush copolymer dissolved in borate-buffered saline (BBS) containing 300 ppm EDTA. The blisters are sealed with foil lidstock and autoclaved at 121° C. for 30 minutes.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biomedical device having a coating on a surface thereof, the coating comprising a brush copolymer comprising (a) monomeric units derived from an ethylenically unsaturated monomer containing one or more boronic acid moieties and; and (b) monomeric units derived from an ethylenically unsaturated hydrophilic macromonomer, wherein the hydrophilic macromonomer comprises units derived from a hydrophilic monomer selected from the group consisting of vinyl lactam, amide, polymerizable amine, vinyl carbonate, vinyl carbamate, oxazolone monomer and mixtures thereof.

2. The biomedical device of claim 1, wherein the brush copolymer has a backbone of the monomeric units derived from an ethylenically unsaturated monomer containing one or more boronic acid moieties; and bristles of the monomeric units derived from the ethylenically unsaturated hydrophilic macromonomer.

3. The biomedical device of claim 1, wherein the ethylenically unsaturated monomer containing one or more boronic acid moieties comprises an ethylenically unsaturated containing aryl boronic acid.

4. The biomedical device of claim 1, wherein the ethylenically unsaturated monomer containing one or more boronic acid moieties is selected from the group consisting of 4-vinylphenylboronic acid, 3-methacrylamidophenylboronic acid, 3-acrylamidophenylboronic acid and mixtures thereof.

5. The biomedical device of claim 1, wherein the hydrophilic macromonomer is made using ATRP or RAFT polymerization.

6. The biomedical device of claim 1, wherein the hydrophilic macromonomer has a number average molecular weight of about 500 to about 200,000.

7. The biomedical device of claim 1, wherein the brush copolymer further comprises monomeric units derived from an ethylenically unsaturated monomer containing a tertiary-amine moiety.

8. The biomedical device of claim 1, wherein the brush copolymer further comprises monomeric units derived from an ethylenically unsaturated monomer containing a hydrophilic moiety capable of rendering the brush copolymer water-soluble.

9. The biomedical device of claim 2, wherein the backbone further comprises monomeric units derived from an ethylenically unsaturated monomer containing a tertiary-amine moiety; and monomeric units derived from an ethylenically unsaturated monomer containing a hydrophilic moiety capable of rendering the brush copolymer water-soluble.

10. The biomedical device of claim 1, wherein the brush copolymer comprises about 1 to about 20 mole percent of the boronic acid-containing monomeric units, about 1 to about 20 mole percent of the monomeric units derived from the ethylenically unsaturated hydrophilic macromonomer, about 1 to about 20 mole percent of monomeric units derived from an ethylenically unsaturated monomer containing a tertiary-amine moiety, and about 40 to about 90 mole percent of monomeric units derived from an ethylenically unsaturated monomer containing a hydrophilic moiety capable of rendering the brush copolymer water-soluble.

11. The biomedical device of claim 1, wherein the biomedical device is an ophthalmic lens.

12. The biomedical device of claim 11, wherein the ophthalmic lens is a contact lens or an intraocular lens.

* * * * *